US008163270B2

(12) United States Patent
Harrington et al.

(10) Patent No.: US 8,163,270 B2
(45) Date of Patent: Apr. 24, 2012

(54) METHODS OF DIAGNOSING AND TREATING MIGRAINE

(75) Inventors: Michael G. Harrington, La Canada, CA (US); Alfred N. Fonteh, Quartz Hill, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 383 days.

(21) Appl. No.: 12/298,254

(22) PCT Filed: Apr. 24, 2007

(86) PCT No.: PCT/US2007/009998
§ 371 (c)(1),
(2), (4) Date: Jun. 17, 2009

(87) PCT Pub. No.: WO2007/127237
PCT Pub. Date: Nov. 8, 2007

(65) Prior Publication Data
US 2009/0318374 A1 Dec. 24, 2009

Related U.S. Application Data

(60) Provisional application No. 60/794,965, filed on Apr. 25, 2006.

(51) Int. Cl.
*A61B 5/055* (2006.01)
(52) U.S. Cl. ...................................................... 424/9.3
(58) Field of Classification Search .................. None
See application file for complete search history.

(56) References Cited

U.S. PATENT DOCUMENTS

| 5,872,103 | A | 2/1999 | Belletti |
| 6,742,221 | B2 | 6/2004 | Lu et al. |
| 2003/0229029 | A1 | 12/2003 | Laudadio et al. |
| 2007/0196479 | A1 | 8/2007 | Willmann et al. |

FOREIGN PATENT DOCUMENTS

| WO | WO-01/59461 A2 | 8/2001 |
| WO | WO-01/59461 A3 | 8/2001 |
| WO | WO-2005/102371 A2 | 11/2005 |
| WO | WO-2005/102371 A3 | 11/2005 |
| WO | WO-2007/127237 A2 | 11/2007 |
| WO | WO-2007/127237 A3 | 11/2007 |
| WO | WO-2009/100370 A1 | 8/2009 |

OTHER PUBLICATIONS

Harrington et al. Cerebrospinal Fluid Sodium Increases in Migraine, Jul.-Aug. 2006, Headache 46(7):1128-1135.*
Altsadhaug, K. et al. (Sep. 2007). "Insomnia and Circadian Variation of Attacks in Episodic Migraine," *Headache* 47:1184-1188.
Arunagiri, G. et al. (2003). "Migraine: An Ophthalmologists Perspective," *Curr. Opin. Opthalmol* 14:344-352.
Barrie, M. (1967). "A Pharmacological Investigation of Cerebro-Spinal Fluid from Patients with Migraine," *Brain* 90(4):785-794.
Brainard, J.B. (Apr. 1976). "Salt Load as Trigger for Migraine," *Minnesota Medicine* 59(4):232-233.
Bruguerolle, B. et al. (2007, e-pub. Jul. 13, 2007). "Rhythmic Pattern in Pain and Their Chronotherapy," *Advanced Drug Delivery Reviews* 59:883-895.
Campbell, D.A. et al. (Dec. 15, 1951). "An Investigation of the Salt and Water Balance in Migraine," *British Medical Journal* 2:1424-1429.
Fischer, H.P. et al. (Jun. 1998). "A Possible Role for Saliva as a Diagnostic Fluid in Patients With Chronic Pain," *Seminars in Arthritis and Rheumatism* 27(6):348-359.
Fox, A.W. et al. (Jun. 1998). "Migraine Chronobiology," *Headache* 38:436-441.
Goldstein, J. et al. (Sep. 2005). "Acetaminophen, Aspirin, and Caffeine Versus Sumatriptan Succinate in the Early Treatment of Migraine: Results From the ASSET Trial," *Headache* 45(8):973-982.
Harrington, M.G. et al. (Jul./Aug. 2006). "Cerebrospinal Fluid Sodium Increases in Migraine," *Headache* 46(7):1128-1135.
International Search Report mailed on Nov. 12, 2007, for PCT Application No. PCT/US2007/009998, filed on Apr. 24, 2007, 2 pages.
Jakubowski, M. et al. (Jul./Aug. 2005). "Terminating Migraine With Allodynia and Ongoing Central Sensitization Using Parenteral Administration of COX1/COX2 Inhibitors," *Headache* 45(7):850-861.
Johansson, B.W. (Mar. 1982). "Migraine: Effect of Digozin," *Journal of the Royal Society of Medicine* 75(3):215-216.
Koenderink, J.B. et al. (2005, e-pub. Jan. 26, 2005). "Na,K-ATPase Mutations in Familial Hemiplegic Migraine Lead to Functional Inactivation," *Biochimica et Biophysica Acta* 1669(1):61-68.
Levi, F. et al. (2007). "Circadian Rhythms: Mechanisms and Therapeutic Implications," in *Annual Review of Pharmacology and Toxicology*, Arthur K. Cho et al. eds., Annual Reviews: Palo Alto, Ca, 47:593-628.
Lipton, R.B. et al. (Apr. 2005). "Aspirin is Efficacious for the Treatment of Acute Migraine," *Headache* 45:283-292.
Lipton, R.B. et al. (Jan. 30, 2007). "Migraine Prevalence, Disease Burden, and the Need for Preventive Therapy," *Neurology* 68(5):343-349.

(Continued)

*Primary Examiner* — John Ulm
(74) *Attorney, Agent, or Firm* — Morrison & Foerster LLP

(57) ABSTRACT

The present invention provides methods of diagnosing migraine attacks and determining predisposition of an individual to the development of migraine based on sodium level in the cerebrospinal fluid (CSF) and/or brain extracellular fluid. The invention also provides methods of treating migraine, wherein the individual is selected for treatment based in the individual's sodium level in the CSF and/or brain extracellular fluid. The CSF sodium level may be based on the sodium concentration in the saliva.

32 Claims, No Drawings

OTHER PUBLICATIONS

Liu, X. et al. (Dec. 2007). "The Conduct of Drug Metabolism Studies Considered Good Practice (I): Analytical Systems and In Vivo Studies," *Curr. Drug Metab.* 8(8):815-821.

Mathew, N.T. et al. (Mar. 2005). "Evaluating the Triptans," *The American Journal of Medicines* 118(Suppl. 1):28S-35S.

National Institute of Health (Jul. 26, 2006). "Cerebrospinal Fluid Sodium Increases in Migraine," NIH Grant No. R01NS43295, located at <http://www.biomedsearch.com/nih/Cerebropsinal-fluid-sodium-increases-in/16866716.html>, last visited on May 9, 2011, 2 pages.

Poondru, S. et al. (Sep. 2000). "Chronopharmacokinetics of Sumatriptan in Healthy Human Subjects," *J. Pharm. Pharmcol.* 52(9):1085-1090.

Qiu, J. et al. (2005, e-pub. Nov. 26, 2004). "Analysis of Guanidine in High Salt and Protein Matrices by Cation-exchange Chromatography and UV Detection," *J. Chromatogr. A.* 1073(1-2):263-267.

Ravi, K.E. et al. (Jan. 2001). "Hypothalamic Digoxin and Pathophysiology of Migraine," *Neuroscience Research Communications* 28(1):59-74.

Soriani, S. et al. (Nov./Dec. 2006). "Circadian and Seasonal Variation of Migraine Attacks in Children," *Headache* 46:1571-1574.

Written Opinion mailed on Nov. 12, 2007, for PCT Application No. PCT/US2007/009998, filed on Apr. 24, 2007, 9 pages.

Flemming, J.B. et al. (Jun. 2000). "Migraine Aura Without Headache: Prevalence and Risk Factors in a Primary Eye Care Population," *Optometry* 71(6):381-389.

Harrington, M.G. et al. (2011, e-pub. Aug. 4, 2011). "Sodium MRI in a Rat Migraine Model and a Neuron Simulation Study Support a Role for Sodium in Migraine," *Cephalalgia* 0(0):1-12.

Lipton, R.B. et al. (Mar. 2005). "The Epidemiology of Migraine," *The American Journal of Medicine* 118(Suppl. 1):3S-10S.

Silberstein, S.D. et al. (2001), "Migraine: Diagnosis and Treatment," Chapter 9 *in Wolf's Headache and Other Head Pain*, 7$^{th}$ ed. Oxford University Press: New York, NY, pp. 121-126.

* cited by examiner

METHODS OF DIAGNOSING AND TREATING MIGRAINE

CROSS-REFERENCE TO RELATED APPLICATIONS

This application is a National Phase filing under 35 U.S.C. §371 of International Application No. PCT/US2007/009998 having an international filing date of Apr. 24, 2007, which claims priority benefit under 35 U.S.C. §119(e) of U.S. Provisional Patent Application No. 60/794,965, filed Apr. 25, 2006, the entire content of each of which is herein incorporated by reference in their entirety.

GOVERNMENT SUPPORT

This invention was made in part with government support under Grant No. NIH RO1 NS043295 awarded by the National Institutes of Health. The government has certain rights to this invention.

TECHNICAL FIELD

This application pertains to methods of diagnosing and treating migraine. Specifically, the application pertains to methods of diagnosing and treating migraine based on sodium levels in the cerebrospinal fluid, the brain extracellular fluid, and/or the saliva.

BACKGROUND

Migraine is a chronic, episodic, and debilitating primary headache syndrome that affects about 15 to 20% of the world population. Arunagiri et al., *Curr. Opin. Opthalmol* 14:344-352 (2003). Migraine has two main types. One type, migraine without aura (previously known as common migraine), affects about 15% of the population. In migraine without aura, the headache is unilateral, pulsating, and moderate to severe in intensity, and may last a few hours to 3 days. The headache may also be associated with nausea, vomiting, photophobia, phonophobia, and other symptoms. The second type, migraine with aura (previously known as classic migraine), affects about 8% of the population. In migraine with aura, one or more auras, such as visual, somatosensory, and motor symptoms, develop prior to the development of a migraine attack. Migraine without aura and migraine with aura co-occur in 13% of migraineurs.

The two prevailing views of migraine pathophysiology are the neuronal and trigeminovascular theories. In the neuronal hypothesis, cortical spreading depression (CSD), a slowing of electroencephalographic activity that propagates across the cortex at 3-5 mm/min, has been recorded during migraine aura. The trigeminovascular hypothesis asserts that an altered modulation of the perivascular nerves of the intracranial vessels sensitizes the nociceptive perivascular fibers' projection to the trigeminal caudate nucleus, which propagates the headache. The current model of migraine is an integration of these two theories linking the intrinsic brain activity of CSD with trigeminal meningeal afferents. In addition, Moskowitz and colleagues present logic to explain the loss/gain of functions found in two different familial hemiplegic migraine genes with the migraine phenotype. However, the basis for hypersensitivity features of migraine—pain, photophobia, phonophobia, osmophobia, nausea, vomiting, and confusion—remains unexplained.

Calcium channel, sodium transporter, and sodium channel gene mutations have been found in familial hemiplegic migraine. For example, mutations in the slow calcium channel gene (CACNA1A), the $Na^+$, $K^+$-ATPase transporter gene (ATP1A2), or the voltage-gated sodium channel gene (SCN1A) underlie cases of the rare familial hemiplegic migraine. Pharmaceuticals with calcium or sodium channel blocking activities have also been shown to be useful in migraine prophylaxis. Although these studies suggest that ion transport may be implicated in migraine pathogenesis, a link between sodium homeostasis and migraine has never been established.

Campbell and colleagues reported in 1951 that blood sodium levels in migraine are increased, and were accompanied by a decrease in protein that they attributed to overhydration. Campbell et al., *Br. Med. J.* 1951, 4745:1424-1429. The reference used a gavimetric method based on pyroantimonate, which has now been abandoned as being indirect. The reference also did not address variations of sodium levels from circadian rhythm fluctuation, a phenomenon that had not been identified at the time of the study. Meanwhile, Jowett reported that sodium and potassium levels were within normal ranges when measured by flame photometry in cerebrospinal fluids from 20 patients during migraine attack. Jowett, *Brain,* 1967, 90(4):785-94. That study did not compare the levels of well with sick migraineurs, and its controls were ill-defined. Brainard reported salt loading as a trigger of migraine. Brainard J. B., *Minn. Med.* 1976, 59(4):232-233. He correlated this phenomenon with increased plasma angiotensin and aldosterone levels rather than sodium levels. None of these references provide a correlation between sodium level in the brain extracellular fluid/cerebrospinal fluid and migraine.

Use of sodium pump inhibitors to treat various diseases has been disclosed in U.S. Pat. No. 5,872,103, U.S. Pat. Pub. No. 2003/0229029, and WO05/102371.

The disclosures of all publications, patents, patent applications and published patent applications referred to herein are hereby incorporated herein by reference in their entirety.

BRIEF SUMMARY OF THE INVENTION

The present invention provides methods of diagnosing migraine in an individual or determining predisposition of an individual to the development of migraine, wherein the diagnosis or determination is based on the CSF or brain extracellular fluid sodium level of the individual. In some embodiments, the method is for diagnosing migraine attack in an individual exhibiting one or more symptoms of migraine. In some embodiments, the method is for determining predisposition of an individual to the development of migraine.

In one aspect, the invention provides methods of diagnosing and treating migraine attack. In some embodiments, the invention provides a method of diagnosing migraine attack in an individual exhibiting one or more symptoms of migraine (such as headache), comprising comparing the cerebrospinal fluid (CSF) sodium level in the individual with the CSF sodium level in the same individual at a symptom free stage, wherein an increase in CSF sodium level above the level at a symptom free stage is indicative of a migraine attack. In some embodiments, the invention provides a method of diagnosing migraine attack in an individual exhibiting one or more symptoms of migraine (such as headache), comprising: a) determining the CSF sodium level in the individual, and b) comparing the CSF sodium level in the individual with the CSF sodium level in the same individual at a symptom free stage, wherein an increase in CSF sodium level above the level at a symptom free stage is indicative of a migraine attack. In some embodiments, the invention provides a method of diagnosing migraine attack in an individual exhibiting one or more symptoms of migraine (such as headache), comprising: a) comparing the CSF sodium level in the individual with the CSF sodium level in the same individual at a symptom free stage, and b) determining whether the individual has a migraine attack based on an increase in CSF sodium level above the level at a symptom free stage. In some embodiments, there is provided a method of providing information for diagnosis of a migraine attack in an individual exhibiting one or more symptoms of migraine (such as headache), comprising: a) determining the CSF sodium level in the individual, and b) providing information about the CSF sodium level of the individual, wherein an increase in CSF sodium level above the level at a symptom free stage is indicative of a migraine attack.

In some embodiments, the CSF sodium level is based on the sodium concentration in the CSF of the individual. In some embodiments, an increase in sodium concentration in the CSF by at least about any of 1 mmol/L, 2 mmol/L, 3 mmol/L, 4 mmol/L, 5 mmol/L, 6 mmol/L, 7 mmol/L, 8 mmol/L, 9 mmol/L, 10 mmol/L, or more is indicative of a migraine attack. In some embodiments, an increase in sodium concentration by at least about any of 0.5%, 1.0%, 1.5%, 2.0%, 2.5%, 3.0%, or more is indicative of a migraine attack. In some embodiments, the increase in CSF sodium level is based on the increase in molar ratio of sodium to another analyte (such as potassium ion) in the CSF of the individual.

In some embodiments, the CSF sodium level is based on the sodium concentration in saliva of the individual. For example, in some embodiments, the invention provides a method of diagnosing migraine attack in an individual exhibiting one or more symptoms of migraine (such as headache), comprising comparing the saliva sodium concentration in said individual with the saliva sodium concentration in the same individual at a symptom free stage, wherein an increase in saliva sodium concentration above the level at the symptom free stage is indicative of a migraine attack. In some embodiments, an increase in sodium concentration in saliva by at least about any of 1, 2, 3, 4, 5, 6, 7, 8, 9, 10, 15, 20, 25, or 30 mmol/L is indicative of a migraine attack. In some embodiments, an increase in saliva sodium concentration by at least about any of 5%, 10%, 15%, 20%, 25%, 30%, 40%, 50%, 60%, 70%, 80%, 90%, 100%, 200%, 300%, or more is indicative of a migraine attack. In some embodiments, the increase in CSF sodium level is based on the increase in molar ratio of sodium to another analyte (such as potassium ion) in the saliva of the individual.

In some embodiments, the CSF sodium level is intracranial CSF sodium level. For example, in some embodiments, the invention provides a method of diagnosing migraine attack in an individual exhibiting one or more symptoms of migraine (such as headache), comprising comparing the intracranial CSF sodium level in the individual with the intracranial CSF sodium level in the same individual at a symptom free stage, wherein an increase in intracranial CSF sodium level above the level at a symptom free stage is indicative of a migraine attack. In some embodiments, the intracranial CSF sodium level is based on intracranial sodium concentration determined by brain magnetic resonance spectrometry.

In some embodiments, there is provided a method of diagnosing migraine attack in an individual exhibiting one or more symptoms of migraine (such as headache) comprising comparing the brain extracellular fluid sodium level in said individual with the brain extracellular fluid sodium level in the same individual at a symptom free stage, wherein an increase in brain extracellular fluid sodium level above the level at a symptom free stage is indicative of a migraine attack. In some embodiments, the invention provides a method of diagnosing migraine attack in an individual exhibiting one or more symptoms of migraine (such as headache), comprising: a) determining the brain extracellular fluid sodium level in the individual, and b) comparing the brain extracellular fluid sodium level in the individual with the brain extracellular fluid sodium level in the same individual at a symptom free stage, wherein an increase in brain extracellular fluid sodium level above the level at a symptom free stage is indicative of a migraine attack. In some embodiments, the invention provides a method of diagnosing migraine attack in an individual exhibiting one or more symptoms of migraine (such as headache), comprising: a) comparing the brain extracellular fluid sodium level in the individual with the brain extracellular fluid sodium level in the same individual at a symptom free stage, and b) determining whether the individual has a migraine attack based on an increase in brain extracellular fluid sodium level above the level at a symptom free stage. In some embodiments, there is provided a method of providing information for diagnosis of a migraine attack in an individual exhibiting one or more symptoms of migraine (such as headache), comprising: a) determining the brain extracellular fluid sodium level in the individual, and b) providing information about the brain extracellular fluid sodium level of the individual, wherein an increase in brain extracellular fluid sodium level above the level at a symptom free stage is indicative of a migraine attack.

In some embodiments, the brain extracellular fluid sodium level is based on regional brain tissue sodium concentration. For example, in some embodiments, the invention provides a method of diagnosing migraine attack in an individual exhibiting one or more symptoms of migraine (such as headache), comprising comparing the regional brain tissue sodium concentration in the individual with the regional brain tissue sodium concentration in the same individual at a symptom free stage, wherein an increase in regional brain tissue sodium concentration above the level at a symptom free stage is indicative of a migraine attack. In some embodiments, the regional brain tissue sodium concentration is determined by brain magnetic resonance spectrometry.

The diagnosis methods described herein provide basis for treatment of migraine. Accordingly, in some embodiments, there is provided a method of treating or continuing to treat migraine attack in an individual exhibiting one or more symptoms of migraine (such as headache), comprising administering to the individual an effective amount of a migraine rescue drug (such as a sodium pump inhibitor), wherein determination of migraine attack is based on the comparison between the CSF sodium level (or brain extracellular fluid sodium level) in the individual with the CSF sodium level (or brain extracellular fluid sodium level) in the same individual at a symptom free stage, wherein an increase in CSF sodium level (or brain extracellular fluid level) above the level at a symptom free stage is indicative of a migraine attack. In some embodiments, the invention provides a method of treating or continuing to treat migraine attack in an individual exhibiting one or more symptoms of migraine (such as headache), comprising: a) comparing the CSF sodium level (or brain extracellular fluid level) in the individual with the CSF sodium level (or brain extracellular fluid level) in the individual with the CSF sodium level (or brain extracellular fluid level) in the same individual at a symptom free stage, wherein an increase in the CSF sodium level (or brain extracellular fluid level) above the level at a symptom free stage is indicative of a migraine attack, and b) administering to the individual an effective amount of a migraine rescue drug (such as a sodium pump inhibitor).

In some embodiments, the migraine rescue drug increases the flow of sodium into cells in the brain. In some embodiments, the migraine rescue drug decreases movement of intracellular sodium to the outside of the cell. In some embodiments, the migraine rescue drug is a sodium pump inhibitor. In some embodiments, the sodium pump inhibitor is steroid glycoside. In some embodiments, the steroid glycoside is any of (and in some embodiments selected from the group consisting of) ouabain, dihydroouabain, digoxin, proscillaridin, digitoxin, lanatoside, acetyldigitoxin, digitoxigenin, and digoxigenin. In some embodiments, the steroid glycoside is ouabain. In some embodiments, the steroid glycoside is digoxin. In some embodiments, a single dose of the migraine rescue drug (such as sodium pump inhibitor) is administered.

In another aspect, there is provided a method of determining predisposition of an individual to the development of migraine by monitoring the sodium level in an individual who has been exposed to a challenging condition (such as administration of a challenging agent). For example, in some embodiments, there is provided a method of determining predisposition of an individual to the development of migraine, comprising: a) subjecting the individual to a challenging condition sufficient to trigger migraine at a symptom free stage; b) monitoring the CSF sodium level in said individual for a certain period of time, wherein a characteristic change in the CSF sodium level in the individual is indicative that the individual is predisposed to the development of migraine. In some embodiments, there is provided a method of determining predisposition of an individual to the development of migraine, comprising: a) administering a sufficient amount of a challenging agent to the individual at a symptom free stage; b) monitoring the CSF sodium level in said individual for a certain period of time, wherein a characteristic change in the CSF sodium level in the individual is indicative that the individual is predisposed to the development of migraine. In some embodiments, the method further comprises the step of determining a baseline CSF sodium level in the individual prior to, during, or immediately after subjecting the individual to a challenging condition (such as administering a challenging agent to the individual).

In some embodiments, there is provided a method of determining predisposition of an individual to the development of migraine, comprising monitoring the CSF sodium level in said individual for a certain period of time, wherein said individual has been subject to a challenging condition sufficient to trigger migraine at a symptom free stage, and wherein a characteristic change in the CSF sodium level in the individual is indicative that the individual is predisposed to the development of migraine. In some embodiments, there is provided a method of determining predisposition of an individual to the development of migraine, comprising monitoring the CSF sodium level in said individual for a certain period of time, wherein the individual has been administered with a sufficient amount of a challenging agent at a symptom free stage, and wherein a characteristic change in the CSF sodium level in the individual is indicative that the individual is predisposed to the development of migraine.

In some embodiments, the CSF sodium level is based on the sodium concentration in the CSF of the individual. In some embodiments, the change (such as increase) of CSF sodium level is based on the change (such as increase) of the molar ratio of sodium to another analyte (such as potassium ion) in the CSF of the individual.

In some embodiments, the CSF sodium level is based on the sodium concentration in the saliva of the individual. In some embodiments, the change (such as increase) of CSF sodium level is based on the change (such as increase) of the molar ratio of sodium to another analyte (such as potassium ion) in the saliva of the individual. For example, in some embodiments, there is provided a method of determining predisposition of an individual to the development of migraine, comprising: a) subjecting the individual to a challenging condition sufficient to trigger migraine at a symptom free stage; b) monitoring the saliva sodium concentration in said individual for a certain period of time, wherein a characteristic change in the saliva sodium concentration in the individual is indicative that the individual is predisposed to the development of migraine. In some embodiments, there is provided a method of determining predisposition of an individual to the development of migraine, comprising: a) administering a sufficient amount of a challenging agent to the individual at a symptom free stage; b) monitoring the saliva sodium concentration in said individual for a certain period of time, wherein a characteristic change in the saliva sodium concentration in the individual is indicative that the individual is predisposed to the development of migraine.

In some embodiments, the CSF sodium level is intracranial sodium level, for example the intracranial sodium level determined by brain magnetic resonance spectrometry. For example, in some embodiments, there is provided a method of determining predisposition of an individual to the development of migraine, comprising: a) subjecting the individual to a challenging condition sufficient to trigger migraine at a symptom free stage; b) monitoring the intracranial CSF sodium level in said individual for a certain period of time, wherein a characteristic change in the intracranial CSF sodium level in the individual is indicative that the individual is predisposed to the development of migraine. In some embodiments, there is provided a method of determining predisposition of an individual to the development of migraine, comprising: a) administering a sufficient amount of a challenging agent to the individual at a symptom free stage; b) monitoring the intracranial CSF sodium level in said individual for a certain period of time, wherein a characteristic change in the intracranial CSF sodium level in the individual is indicative that the individual is predisposed to the development of migraine.

In some embodiments, there is provided a method for determining predisposition of an individual to the development of migraine, comprising: a) subjecting the individual to a challenging condition sufficient to trigger migraine at a symptom free stage; b) monitoring the brain extracellular fluid sodium level in said individual for a certain period of time, wherein a characteristic change in the brain extracellular fluid sodium level in the individual is indicative that the individual is predisposed to the development of migraine. In some embodiments, there is provided a method for determining predisposition of an individual to the development of migraine, comprising: a) administering a sufficient amount of a challenging agent to the individual at a symptom free stage; b) monitoring the brain extracellular fluid sodium level in said individual for a certain period of time, wherein a characteristic change in the brain extracellular fluid sodium level in the individual is indicative that the individual is predisposed to the development of migraine.

In some embodiments, there is provided a method of determining predisposition of an individual to the development of migraine, comprising monitoring the brain extracellular fluid sodium level in said individual for a certain period of time, wherein said individual has been subject to a challenging condition sufficient to trigger migraine at a symptom free stage, and wherein a characteristic change in the brain extracellular fluid sodium level in the individual is indicative that the individual is predisposed to the development of migraine. In some embodiments, there is provided a method of determining predisposition of an individual to the development of migraine, comprising monitoring the brain extracellular fluid sodium level in said individual for a certain period of time, wherein the individual has been administered with a sufficient amount of a challenging agent at a symptom free stage, and wherein a characteristic change in the brain extracellular fluid sodium level in the individual is indicative that the individual is predisposed to the development of migraine.

In some embodiments, the brain extracellular fluid sodium level is based on regional brain tissue sodium concentration for example the regional brain tissue sodium concentration as determined by brain magnetic resonance spectrometry. For example, in some embodiments, there is provided a method of determining predisposition of an individual to the development of migraine, comprising: a) subjecting the individual to a challenging condition sufficient to trigger migraine at a symptom free stage; b) monitoring the regional brain tissue sodium concentration in said individual for a certain period of time, wherein a characteristic change in the regional brain tissue sodium concentration in the individual is indicative that the individual is predisposed to the development of migraine. In some embodiments, there is provided a method of determining predisposition of an individual to the development of migraine, comprising: a) administering a sufficient amount of a challenging agent to the individual at a symptom free stage; b) monitoring the regional brain tissue sodium concentration in said individual for a certain period of time, wherein a characteristic change in the regional brain tissue sodium concentration in the individual is indicative that the individual is predisposed to the development of migraine.

In some embodiments, an increase in the CSF sodium level (or brain extracellular fluid sodium level) above a baseline level after a certain time period is indicative that the individual is predisposed to the development of migraine. In some embodiments, an initial drop of the CSF sodium level (or brain extracellular fluid level) below a baseline level followed by a subsequent increase in the CSF sodium level (or brain extracellular fluid level) above the baseline level is indicative that the individual is predisposed to the development of migraine.

In another aspect, there is provided a method of determining predisposition of an individual to the development of migraine, comprising determining the CSF sodium level in said individual, wherein an increase in CSF sodium level above a threshold level is indicative that the individual is predisposed to the development of migraine. In some embodiments, there is provided a method of determining predisposition of an individual to the development of migraine, comprising: a) determining the CSF sodium level in said individual, and b) comparing the CSF sodium level of the individual with a threshold level, wherein an increase in CSF sodium level above a threshold level is indicative that the individual is predisposed to the development of migraine. In some embodiments, there is provided a method of determining predisposition of an individual to the development of migraine, comprising: a) comparing the CSF sodium level of the individual with a threshold level, and b) determining whether the individual is predisposed to the development of migraine based on an increase in CSF sodium level above the threshold level. In some embodiments, there is provided a method of providing information for determining predisposition of an individual to the development of migraine, comprising: a) determining the CSF sodium level in said individual, and b) providing information about CSF sodium level of the individual, wherein an increase in CSF sodium level above a threshold level is indicative that the individual is predisposed to the development of migraine.

In some embodiments, the CSF sodium level is based on the sodium concentration in the CSF of the individual. In some embodiments, the increase in CSF sodium level is based on the increase in molar ratio of sodium to another analyte (such as potassium ion) in the CSF of the individual.

In some embodiments, the CSF sodium level is based on the sodium concentration in saliva of the individual. For example, in some embodiments, there is provided a method of determining predisposition of an individual to the development of migraine, comprising determining saliva sodium concentration in said individual, wherein a saliva sodium concentration above a threshold concentration is indicative that the individual is predisposed to the development of migraine. In some embodiments, the increase in CSF sodium level is based on the increase in molar ratio of sodium to another analyte (such as potassium ion) in the saliva of the individual.

In some embodiments, the CSF sodium level is intracranial CSF sodium concentration. For example, in some embodiments, there is provided a method of determining predisposition of an individual to the development of migraine, comprising determining intracranial CSF sodium concentration in said individual, wherein an intracranial CSF sodium concentration above a threshold concentration is indicative that the individual is predisposed to the development of migraine. In some embodiments, the CSF sodium concentration is determined by brain magnetic spectrometry.

In some embodiments, there is provided a method of determining predisposition of an individual to the development of migraine, comprising determining brain extracellular fluid sodium level in said individual, wherein a brain extracellular fluid sodium level above a threshold level is indicative that the individual is predisposed to the development of migraine. In some embodiments, there is provided a method of determining predisposition of an individual to the development of migraine, comprising: a) determining the brain extracellular fluid sodium level in said individual, and b) comparing the brain extracellular fluid sodium level of the individual with a threshold level, wherein an increase in the brain extracellular fluid sodium level above a threshold level is indicative that the individual is predisposed to the development of migraine. In some embodiments, there is provided a method of determining predisposition of an individual to the development of migraine, comprising: a) comparing the brain extracellular fluid sodium level of the individual with a threshold level, and b) determining whether the individual is predisposed to the development of migraine based on an increase in the brain extracellular fluid sodium level above the threshold level. In some embodiments, there is provided a method of providing information for determining predisposition of an individual to the development of migraine, comprising: a) determining the brain extracellular fluid sodium level in said individual, and b) providing information about the brain extracellular fluid sodium level of the individual, wherein an increase in the brain extracellular fluid sodium level above a threshold level is indicative that the individual is predisposed to the development of migraine.

In some embodiments, the brain extracellular fluid sodium level is based on regional brain tissue sodium concentration as determined by brain magnetic resonance spectrometry. For example, in some embodiments, there is provided a method of determining predisposition of an individual to the development of migraine, comprising determining regional brain tissue sodium concentration in said individual, wherein a regional brain tissue sodium concentration above a threshold concentration is indicative that the individual is predisposed to the development of migraine.

Also provided herein are kits and devices for carrying out one or more methods described herein. Also provided herein are uses of CSF sodium level or brain extracellular extract fluid sodium level for diagnosis of a migraine attack or determination of predisposition of an individual to the development of migraine. It is to be understood that one, some, or all of the properties of the various embodiments described herein may be combined to form other embodiments of the present invention.

DETAILED DESCRIPTION OF THE INVENTION

The present invention is based on an observation that the CSF sodium levels were increased in migraineurs in sick (MH+) state as compared to well (MH−) state. The increase in sodium level was independent from other clinical or pharmacological fluctuations, CSF concentrations of calcium, magnesium, and potassium, as well as blood plasma sodium levels in the individual. We also observed that the saliva sodium concentration increased in a migraineur in sick (MH+) state as compared to well (MH−) state. This correlates well with changes in CSF sodium concentration. In addition, we observed that the CSF sodium levels of migraineurs are statistically higher than those of nonmigraineurs.

We believe that all migraineurs have a common biochemistry distinct from non-migraineurs. This common biochemistry decompensates after different types of migraine triggers (including stress, dietary changes, hormonal changes), and has the following attributes: a) broad distribution and dissemination throughout the brain; b) capacity for immediate response that can be sustained for hours; c) influence by many different triggers; and d) association with many apparently disparate biochemical changes that have been implicated in migraine.

The observed increase in CSF sodium levels in migraineurs in sick state suggests that disturbance of sodium homeostasis is one of the common biochemical mechanisms underlying migraine attacks. CSF sodium equilibrates rapidly with sodium in the brain extracellular fluid, especially in mobile subjects. Thus we can confidently assume that the observed change in CSF sodium level reflects a similar change in sodium level in brain extracellular fluid. Sodium ion and sodium regulatory mechanisms are present throughout the brain, subject to tight physiologic regulation, and influenced by many different factors. Any deviation in $Na^+$ is expected to have a wide and considerable impact on brain functions. For example, an increased extracellular sodium will slightly reduce the threshold for repetitive neuronal firing by increasing $Na^+$ conductance, increase pH-induced nociceptor discharge, and alter coincidence detection in medial superior olivary neurons. These effects would contribute to a substantial neural disturbance that is consistent with the main clinical features of migraine: pain, photophobia, phonophobia, osmophobia, nausea, vomiting, and confusion.

Without wishing to be bound by the theory, it is hypothesized that sodium pumps in the brain are responsible for the increase in the CSF or brain extracellular fluid sodium level, and that all migraineurs have a sodium pump axis that is more sensitive to that of nonmigraineurs. It is further hypothesized that, during migraine, an initial sodium pump competitive inhibition, for example by an endogenous or exogenous substance, results in a low extracelluar sodium level. This low sodium level may lead to symptoms of aura in some individuals. In response to the low extracellular fluid sodium level (and thus an excess of intracellular sodium), more sodium pumps are made, for example by increased transcription, translation, and/or localization. The increase in sodium pump production overcompensates and leads to an increased brain extracellular fluid sodium level and neuronal hyperpolarization that manifests as the migraine attack. The high sodium level is reflected in the CSF, which is in direct communication with the brain extracellular fluid.

The biochemical hypothesis described herein, called "sodium pump hypothesis," fits into: 1) the time course of aura and the sodium biochemistry of CSD; 2) the time course of migraine attack and our observation in CSF sodium levels; and 3) the fact that all known actions of drugs for treatment of migraine directly or close to directly act on sodium pump. This sodium pump hypothesis forms the basis of some aspects/embodiments of the present invention.

Accordingly, the present invention provides methods of diagnosing migraine in an individual or determining predisposition of an individual to the development of migraine, wherein the diagnosis or determination is based on the CSF or brain extracellular fluid sodium level of the individual. In some embodiments, the method is for diagnosing migraine attack in an individual exhibiting one or more symptoms of migraine. In some embodiments, the method is for determining predisposition of an individual to the development of migraine.

In one aspect, there is provided a method of diagnosing migraine attack in an individual exhibiting one or more symptoms of migraine (such as headache), comprising comparing the CSF sodium level (or brain extracellular fluid sodium level) in said individual with the CSF sodium level (or brain extracellular fluid sodium level) in the same individual at a symptom free stage, wherein an increase in CSF sodium level (or brain extracellular fluid sodium level) above the level at a symptom free stage is indicative of a migraine attack. In some embodiments, the CSF sodium level is based on sodium concentration in the saliva of the individual.

Also provided is a method of treating or continuing to treat migraine attack in an individual exhibiting one or more symptoms of migraine (such as headache), comprising administering to the individual an effective amount of a migraine rescue drug (such as sodium pump inhibitor), wherein determination of migraine attack is based on the comparison between the CSF sodium level (or brain extracellular fluid sodium level) in the individual with the CSF sodium level (or brain extracellular fluid sodium level) in the same individual at a symptom free stage, wherein an increase in CSF sodium level (or brain extracellular fluid sodium level) above the level at a symptom free stage is indicative of a migraine attack. In some embodiments, the CSF sodium level is based on sodium concentration in the saliva of the individual.

In another aspect, there is provided a method of determining predisposition of an individual to the development of migraine, comprising: a) subjecting the individual to a challenging condition sufficient to trigger migraine at a symptom free stage; b) monitoring the CSF sodium level (or brain extracellular fluid sodium level) in said individual for a certain period of time, wherein a characteristic change in the CSF sodium level (or brain extracellular fluid sodium level) in the individual is indicative that the individual is predisposed to the development of migraine. In some embodiments, the CSF sodium level is based on sodium concentration in the saliva of the individual.

In another aspect, there is provided a method of determining predisposition of an individual to the development of migraine, comprising determining CSF sodium level (or brain extracellular fluid sodium level) in said individual, wherein an increase in CSF sodium level (or brain extracellular fluid sodium level) above a threshold level is indicative that the individual is predisposed to the development of migraine. In some embodiments, the CSF sodium level is based on sodium concentration in the saliva of the individual.

It is understood that aspects and embodiments of the invention described herein include "consisting" and/or "consisting essentially of" aspects and embodiments.

Reference to "about" a value or parameter herein includes (and describes) embodiments that are directed to that value or parameter per se. For example, description referring to "about X" includes description of "X."

As used herein and in the appended claims, the singular forms "a," "or," and "the" include plural referents unless the context clearly indicates otherwise.

Methods of Diagnosis and Treating Migraine Attack

Diagnosis of Migraine Attack

The invention in one aspect provides a method of diagnosing migraine attack in an individual. Following the establishment of a baseline CSF sodium level in an individual at a symptom free stage, variation of CSF sodium level in conjunction with one or more symptoms of migraine can serve as an indication of a migraine attack. The diagnosis methods described herein provide sufficient warning for the individual to take suitable steps to minimize the effect or at least moderate the severity of a migraine attack, for example, by administering a migraine rescue drug, such as sodium pump inhibitors described below.

Accordingly, in some embodiments, the invention provides a method of diagnosing migraine attack in an individual exhibiting one or more symptoms of migraine (such as headache), comprising comparing the CSF sodium level (or brain extracellular fluid sodium level) in said individual (referred to herein as "symptom-associated sodium level") with the CSF sodium level (or brain extracellular fluid sodium level) in the same individual at a symptom free stage (referred to herein as "symptom-free sodium level"), wherein an increase in CSF sodium level (or brain extracellular fluid sodium level) above the level at a symptom free stage is indicative of a migraine attack. In some embodiments, the invention provides a method of diagnosing migraine attack in an individual exhibiting one or more symptoms of migraine (such as headache), comprising: a) determining the CSF sodium level (or brain extracellular fluid sodium level) in said individual; and b) comparing the CSF sodium level (or brain extracellular fluid sodium level) in said individual with the CSF sodium level (or brain extracellular fluid sodium level) in the same individual at a symptom free stage, wherein an increase in CSF sodium level (or brain extracellular fluid sodium level) above the level at a symptom free stage is indicative of a migraine attack. In some embodiments, the method further comprises the step of determining the CSF sodium level (or brain extracellular fluid sodium level) in the individual at a symptom free stage.

In some embodiments, the invention provides a method of diagnosing migraine attack in an individual exhibiting one or more symptoms of migraine (such as headache), comprising: a) comparing the CSF sodium level (or brain extracellular fluid sodium level) in the individual with the CSF sodium level (or brain extracellular fluid sodium level) in the same individual at a symptom free stage, and b) determining whether the individual has a migraine attack based on an increase in CSF sodium level (or brain extracellular fluid sodium level) above the level at a symptom free stage. In some embodiments, there is provided a method of providing information for diagnosis of a migraine attack in an individual exhibiting one or more symptoms of migraine (such as headache), comprising: a) determining the CSF sodium level (or brain extracellular fluid sodium level) in the individual, and b) providing information about the CSF sodium level (or brain extracellular fluid sodium level) of the individual, wherein an increase in CSF sodium level above the level at a symptom free stage is indicative of a migraine attack.

An "individual" is a vertebrate, preferably a mammal, more preferably a human. Mammals include, but are not limited to, farm animals, sport animals, pets, primates, mice and rats. In some embodiments, the individual is human. In some embodiments, the individual has a prior history of migraine attack(s). In some embodiments, the individual has previously been diagnosed (for example diagnosed based on the International Headache Classification standard) with one or more of the following: migraine with aura, migraine without aura, migraine with prolonged aura, migrainous infarction, opthalmoplegic migraine, basilar migraine, familial hemiplegic migraine, and retinal migraine. In some embodiments, the individual is a woman. In some embodiments, the individual is a woman having history of menstrual migraine or menstrual associated migraine.

In some embodiments, the individual is an individual other than human. In some embodiments, the individual is an animal model for the study of migraine. Animal models for migraine studies are known in the art. See, for example, Goadsby, *Migraine and Headache Pathophysiology*, Martin Dunitz, Ltd. 1999.

An individual "exhibiting one or more symptoms of migraine" used herein refers to an individual exhibiting one or more symptoms associated with a migraine attack. Symptoms associated with a migraine attack include, but are not limited to, headache, nausea, vomiting, photophobia, phonophobia, osmophobia, vertigo, and allodynia. In some embodiments, the individual exhibits a headache. In some embodiments, the individual exhibits a headache that is of moderate intensity. In some embodiments, the individual exhibits a headache that is of severe intensity. In some embodiments, the individual exhibits a headache with a severity of more than about any of 1, 2, 3, 4, 5, 6, 7, 8, 9, or 10 on a scale of 0 to 10. In some embodiments, the individual has had an aura prior to exhibiting a symptom of migraine. In some embodiments, the individual has not had an aura prior to exhibiting a symptom of migraine.

An individual is "at a symptom free stage" when the individual is not exhibiting one or more symptom(s) associated with a migraine attack. The individual may have one or more symptoms of aura, including, for example, any of visual symptoms, somatosensory symptoms, as well as other neurologic manifestations such as motors symptoms, hemispheric symptoms (including hemiparesis, dysarthria, and clumsiness), and speech difficulties. In some embodiments, the individual has no symptom of an aura.

"CSF sodium level," or "sodium level in the CSF" refers to the level of sodium ion in the cerebrospinal fluid. As will be appreciated by a person skilled in the art, the CSF sodium level need not be measured in absolute terms, although this can of course be done if desired. Generally, it will be sufficient to assay sodium in a manner which yields a data or signal that relates to the actual sodium concentration in the CSF, so that such data or signal can be compared with similar data or signal obtained as a baseline or threshold level to determine whether or not a change has occurred. In some embodiments, the CSF sodium level is determined by an in vitro assay.

In some embodiments, the CSF sodium level is based on the sodium concentration in the CSF. For example, in some embodiments, an increase in CSF sodium concentration by at least about 1 mmol/L, such as at least about any of 2 mmol/L, 3 mmol/L, 4 mmol/L, 5 mmol/L, 6 mmol/L, 7 mmol/L, 8 mmol/L, 9 mmol/L, 10 mmol/L, or more is indicative of a migraine attack. In some embodiment, an increase in CSF sodium concentration by at least about 3 mmol/L is indicative of a migraine attack. In some embodiments, an increase in CSF sodium concentration by at least about any of 0.5%, 1.0%, 1.5%, 2.0%, 2.5%, 3.0%, or more is indicative of a migraine attack. In some embodiments, the increase in CSF sodium level is based on the increase in the ratio of the CSF sodium concentration to the concentration of another analyte (such as another cation) in the CSF. In some embodiments, the concentration of the other analyte in the CSF remains unchanged during a migraine attack. In some embodiments, the increase in CSF sodium level is based on the increase in molar ratio of sodium to potassium ions in the CSF. In some embodiments, the increase in CSF sodium level is based on the increase in molar ratio of sodium to calcium ions in the CSF. In some embodiments, the increase in CSF sodium level is based on the increase in molar ratio of sodium to magnesium ions in the CSF. In some embodiments, the increase in CSF sodium level is based on the increase in ratio of the sodium concentration and the total protein concentration in the CSF. In some embodiments, the increase in CSF sodium level is based on the increase in ratio of the sodium concentration and the concentration of a particular protein in the CSF, such as albumin, immunoglobulin, transferrin, $\alpha$-1-antitrypsin, and transthyretin. Other analytes in the CSF may also be used for the determination of a ratio. In some embodiment, the increase in CSF sodium level is based on the increase in ratio of the CSF sodium concentration and the plasma sodium concentration.

In some embodiments, the CSF used for determination of sodium level is taken from the lumbar site. In some embodiments, the CSF used for determination of sodium level is taken from the cervical site. In some embodiments, the CSF is taken from the ventricular site. In some embodiments, the intracranial CSF sodium level is determined, for example, by brain magnetic resonance spectrometry.

The CSF sodium level can also be determined based on the sodium level in a body fluid which correlates with the CSF sodium level. The sodium level in a body fluid "correlates" with the CSF sodium level when a change in sodium level in the body fluid corresponds (in same or different magnitude) to that of the CSF sodium level. For example, in some embodiments, the CSF sodium level is determined on the basis of sodium concentration in the saliva of the individual. We have observed an increase in saliva sodium level in an individual during migraine attack as compared to that of the same individual without migraine attack. This correlates with changes in the CSF. Accordingly, the present invention contemplates determination of saliva sodium level as an unintrusive alternative for the determination of CSF sodium level. The saliva can be collected by spitting method, or collected from stimulated salivary gland. Methods of collecting saliva are also disclosed in Fischer et al., *Seminars in Arthritis and Rheumatism*, 1998, 27(6):348-359. Analysis of sodium level can be determined in vitro.

In some embodiments, the sodium concentration in saliva is used as a basis for the determination of a CSF sodium level. In some embodiments, an increase in saliva sodium concentration by at least about 1 mmol/L, such as at least about any of 2 mmol/L, 3 mmol/L, 4 mmol/L, 5 mmol/L, 6 mmol/L, 7 mmol/L, 8 mmol/L, 9 mmol/L, 10 mmol/L, 15 mmol/L, 20 mmol/L, 25 mmol/L, 30 mmol/L, or more is indicative of a migraine attack. In some embodiment, an increase in saliva sodium concentration by at least about 4 mmol/L is indicative of a migraine attack. In some embodiments, an increase in saliva sodium concentration by at least about any of 5%, 10%, 15%, 20%, 25%, 30%, 40%, 50%, 60%, 70%, 80%, 90%, 100%, 200%, 300%, or more is indicative of a migraine attack. In some embodiments, the increase in sodium level is based on the increase in ratio of the saliva sodium concentration to concentration of another analyte (such as another cation) in the saliva. In some embodiments, the level of the other analyte in the saliva remains unchanged during a migraine attack. In some embodiments, the increase in CSF sodium level is based on the increase in molar ratio of sodium to potassium ions in the saliva. In some embodiments, the increase in CSF sodium level is based on the increase in molar ratio of sodium to calcium ions in the saliva. In some embodiments, the increase in CSF sodium level is based on the increase in molar ratio of sodium to magnesium ions in the saliva. In some embodiments, the increase in CSF sodium level is based on the increase in ratio of the sodium concentration and the total protein concentration in the saliva. In some embodiments, the increase in CSF sodium level is based on the increase in ratio of the sodium concentration and the concentration of a particular protein in the saliva, such as salivary amylase and lactoferrin. Other analytes in the saliva may also be used for the determination of a ratio. In some embodiments, the increase in CSF sodium level is based on the increase in ratio of the saliva sodium concentration and the plasma sodium concentration.

In some embodiments, the CSF sodium level is based on sodium concentration in a body fluid produced by a gland that is innervated by neuronal terminals originating from trigeminovascular system. In some embodiments, the increase in CSF sodium level is based on the increase in molar ratio of sodium to another analyte in a body fluid produced by a gland that is innervated by neuronal terminals originating from trigeminovascular system. For example, the sodium level can be based on sodium concentration in tear, saliva, sweat, nasal discharge, etc. In some embodiments, sodium level is based on sodium concentration in a body fluid that is produced by a gland that is of the neuroectoderm origin. In some embodiments, the increase in CSF sodium level is based on the increase in molar ratio of sodium to another analyte in a body fluid that is produced by a gland that is of the neuroectoderm origin.

In some embodiments, the sodium level in the brain extracellular fluid is used for diagnosis. Brain extracellular fluid sodium level can be based on regional brain tissue sodium concentration for example regional brain tissue sodium concentration as determined by brain magnetic resonance spectrometry.

A comparison between the symptom-associated sodium level and the symptom-free sodium level needs to take circadian sodium fluctuation into account. Typically in an individual not exhibiting symptom(s) of migraine, the CSF level is relatively stable from about 6 AM to about 6 PM, increases from about 6 PM, peaks at about midnight, and drops to a low level at about 6 AM. To minimize the interference of such fluctuation in sodium level, it is desirable that determination of the symptom-associated sodium level and the symptom-free sodium level be made at the same time on different days, or during the same time period of the same on different day(s) when normal sodium level is relatively stable. For example, in some embodiments, both the symptom-associated sodium level and the symptom-free sodium level are determined during the time period of about 6 AM to about 6 PM. In some embodiments, both the symptom-associated sodium level and the symptom-free sodium level are determined during the time period of any of about 1 PM to about 6 PM, about 1 PM to about 5 PM, or about 2 PM to about 4 PM. In some embodiments, a symptom-free sodium level is established several days, several weeks or even several months before measurement of the symptom-associated sodium level for diagnosis. In some embodiments, a symptom-free sodium level is measured in the same day as the measurement of the symptom-associated sodium level (i.e., within the same time period in the same day). In some embodiments, a series of symptom-free sodium levels are established by measuring sodium levels at different time points of a day and, depending on the timing of the measurement of the symptom-associated sodium level, a corresponding symptom-free sodium level of the individual can be chosen for the comparison. In some embodiments, there is no change in medication during the time period between the symptom-free sodium level determination and the symptom-associated sodium level determination. In some embodiments, there is no change in sleep, diet (including caffeine and alcohol), and/or stress level during the time period between the symptom-free sodium level determination and the symptom-associated sodium level determination.

Treatment of Migraine Attack

The present invention also provides methods of treating migraine attack, wherein the CSF sodium level (or brain extracellular fluid sodium level) is used as a basis for selecting the individual to receive or continue to receive treatment. Specifically, CSF sodium level or brain extracellular fluid sodium level may be used as a basis by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probably or likely unsuitability of an individual to continue to receive treatment(s); (f) adjusting dosage(s); (g) predicting likelihood of clinical benefits. As would be well understood by one in the art, measurement of CSF sodium level of brain extracellular fluid sodium level is a clear indication that this parameter is used as a basis for initiating, continuing, adjusting and/or ceasing administration of the treatments described herein.

In some embodiments, there is provided a method of treating or continuing to treat migraine attack in an individual exhibiting one or more symptoms of migraine (such as headache), comprising administering to the individual an effective amount of a migraine rescue drug (such as sodium pump inhibitor), wherein determination of migraine attack is based on the comparison between the CSF sodium level (or brain extracellular fluid sodium level) in the individual with the CSF sodium level (or brain extracellular fluid sodium level) in the same individual at a symptom free stage, wherein an increase in CSF sodium level (or brain extracellular fluid sodium level) above the level at a symptom free stage is indicative of a migraine attack. In some embodiments, there is provided a method of treating or continuing to treat migraine attack in an individual exhibiting one or more symptoms of migraine (such as headache), comprising: a) comparing the CSF sodium level (or brain extracellular fluid sodium level) in the individual with the CSF sodium level (or brain extracellular fluid sodium level) of the same individual at a symptom free stage, wherein an increase in CSF sodium level or brain extracellular fluid sodium level is indicative of a migraine attack; and b) administering to the individual an effective amount of a migraine rescue drug (such as a sodium pump inhibitor) to the individual.

As used herein, "treatment" is an approach for obtaining beneficial or desired results including clinical results. For purpose of this invention, beneficial or desired clinical results include, but are not limited to, one or more of the following: reducing severity of migraine attack, shortening the duration migraine attack, relieving or reducing one or more symptoms of migraine attack, and stabilizing (i.e., not worsening) one or more symptoms of migraine attack. Symptoms of migraine attack include, for example, headache, nausea, vomiting, photophobia, phonophobia, osmophobia, vertigo, and allodynia.

An "effective amount" is an amount sufficient to effect beneficial or desired results including clinical results. An effective amount can be administered in one or more administrations. For purpose of treating migraine attack, an effective amount is an amount sufficient to reduce severity of migraine attack, shorten the duration of migraine attack, relieve or reduce one or more symptoms of migraine attack, or stabilize (i.e., not worsen) one or more symptoms of migraine attack.

"Migraine rescue drug" used herein refers to drugs useful for rescue treatment of migraine attacks. In some embodiments, the migraine rescue drug directly or indirectly corrects (i.e., decreases) the elevated brain extracellular fluid sodium. For example, in some embodiments, the migraine rescue drug increases the flow of sodium into cells in the brain. In some embodiments, the migraine rescue drug decreases the movement of intracellular sodium to the extracellular fluid. In some embodiments, the migraine rescue drug is any of (and in some embodiments selected from the group consisting of): sodium pump inhibitors, anticonvulsants (including for example valproic acid and topiramate), analgesics (including for example ibuprofen, naproxen, ketorolac, methadone, hydrocodone, and meperidine), antiemetics (including for example prochlorperazine), ergot derivatives (including for example ergotamine), triptans (including for example sumatriptan, rizatriptan, naratriptan, zolmitriptan, eletriptan, almotriptan, and frovatriptan), neuropeptide antagonists (including for example CGRP antagonist such as BIBN4096BS), barbiturates (including for example phenobarbitone), Midrin®, methysergide, isometheptene, gabapentin, pregabalin, and combination drugs such as Fioricet®, Esgic®, Tylenol No. 3, and Fiurinal. Other migraine rescue drugs are known in the art. See, for example, Goldstein et al., *Headache,* 2005, 45(7): 850-61; Goldstein et al., *Headache,* 2005, 45(8):973-82.

In some embodiments, the migraine rescue drug is a sodium pump inhibitor. Sodium pump, also referred to as the $Na^+$—$K^+$-ATPase, is a highly-conserved integral membrane protein that is expressed in virtually all cells of higher organisms. It has been estimated that roughly 25% of all cytoplasmic ATP is hydrolyzed by sodium pumps in resting humans. In nerve cells, approximately 70% of the ATP is consumed to fuel sodium pumps. A "sodium pump inhibitor" is a compound that inhibits the function or activity of a sodium pump.

In some embodiments, the sodium pump inhibitor is a steroid glycoside. Steroid glycosides are found in a number of plants, insects, and in the venom of certain toads. They have also been isolated from mammals. Steroid glycosides are also called cardiac glycosides because they have been used extensively to treat heart failures, presumably by inhibiting the sodium pump. These compounds typically have a sugar (glycoside) portion and an aglycone (steroid) portion. The R group at the 17-position of the aglycone portion defines the class of steroid glycoside. Two classes have been observed in nature—the cardenolides and the bufadienolides. The cardenolides have an unsaturated butyrolactone ring while the bufadienolides have an apyrone ring. The aglycone derivatives of steroid glycosides have a similar structure, but lack the carbohydrate characteristics of the steroid glycoside.

These aglycone derivatives are also useful for the present invention, and the term "steroid glycoside" is used broadly herein to also encompass aglycone derivatives.

Suitable steroid glycosides for the present invention include, but are not limited to, ouabain, dihydroouabain, digoxin, proscillaridin, digitoxin, lanatoside, acetyldigitoxin, digitoxigenin, digoxigenin, digitalis, strophanthin, digitoxose, cardenolide, oleandrin, acovenoside, gitalin, gitoxin, tigonin, gitonin, deslanoside, digilanides, chansu, and derivatives thereof. In some embodiments, the steroid glycoside is any of (and in some embodiments selected from the group consisting of) ouabain, dihydroouabain, digoxin, proscillaridin, digitoxin, lanatoside, acetyldigitoxin, digitoxigenin, and digoxigenin. In some embodiments, the steroid glycoside is ouabain. In some embodiments, the steroid glycoside is digoxin. These steroid glycoside may either derive from natural sources or be synthetically produced. For example, in some embodiments, the steroid glycoside is purified from plants or other organisms (such as toads or mammals). In some embodiments, the steroid glycoside is an ouabain-like or digoxin-like molecule found in human or an analog thereof.

The migraine rescue drug (such as sodium pump inhibitor) can be administered via a variety of routes, including, for example, oral, nasal, inhalational, parental, intravenous, intraperitoneal, subcutaneous, intramuscular, intradennal, topical, rectal, etc. The migraine rescue drug (such as sodium pump inhibitor) may also be administered directly to the nervous system, for example, by any of intracerebral, intraventricular, intracerebroventricular, intrathecal, intracisternal, intraspinal, and/or perispinal route. In some embodiments, the migraine rescue drug (such as sodium pump inhibitor) is administered orally. In some embodiments, the migraine rescue drug (such as sodium pump inhibitor) is administered nasally. In some embodiments, the migraine rescue drug (such as sodium pump inhibitor) is administered intravenously. In some embodiments, the migraine rescue drug (such as sodium pump inhibitor, for example digioxin or ouabain) is administered over more than about any of 2, 3, 4, 5, 6, 7, 8, 9, 10, 12, or 15 minutes.

In some embodiments, the migraine rescue drug (such as sodium pump inhibitor) is administered neat. In some embodiments, the migraine rescue drug (such as sodium pump inhibitor) is administered along with a pharmaceutically acceptable excipient, and may be in various formulations. Pharmaceutically acceptable excipients are known in the art, and are relatively inert substances that facilitate administration of the pharmacologically effective substance. For example, an excipient can give form or consistency, or act as a diluent. Suitable excipients include, but are not limited to, stabilizing agents, wetting and emulsifying agents, salts for varying osmolarity, encapsulating agents, and buffers.

The particular dosage of the migraine rescue drug (such as sodium pump inhibitor) will depend on the particular drug (or sodium pump inhibitor). Empirical consideration, such as the half life of the sodium pump inhibitor, generally will contribute to the determination of the dosage. The dosage also depends on the route of administration. Generally, a dosage of about 1 ng to about 100 µg per kilogram body weight is administered. In some embodiments, the dosage is about any of 1, 2, 3, 4, 5, 6, 7, 8, 9, 10, 20, 30, 40, or 50 µg per kilogram body weight. For example, the dosage of a sodium pump inhibitor (such as steroid glycoside, for example ouabain or digioxin) can be about any of 1, 2, 3, 4, 5, 6, 7, 8, 9, 10, 20, 30, 40, or 50 µg per kilogram body weight. In some embodiments, the migraine rescue drug (such as sodium pump inhibitor) is administered in an amount that results in a serum level of about any of 0.1, 0.3, 0.5, 0.8, 1.0, 1.3, 1.5, 1.8, 2.0, 2.3, 2.5, 2.8, 3.0 ng/mL, or more.

Typically, the migraine rescue drug (such as sodium pump inhibitor) is administered shortly after diagnosis of a migraine attack. For example, in some embodiments, the migraine rescue drug (such as sodium pump inhibitor) is administered within about any of 5, 10, 15, 20, 30, 40, 50, 60, 70, 80, 90, 100, or 120 minutes after diagnosis of a migraine attack. In some embodiments, a single dose of an effective amount of the migraine rescue drug (such as sodium pump inhibitor) is administered. In some embodiments, multiple doses of migraine rescue drug (such as sodium pump inhibitor) are administered. The time intervals between these multiple doses can be, for example, any of 2, 4, 6, 8, 10, or more hours. In some embodiments, the method further comprises continuing to monitor CSF sodium level or brain extracellular fluid sodium level after the administration of the migraine rescue drug (such as sodium pump inhibitor). The sodium levels can be used, for example, as a basis for: a) continuing the treatment; b) discontinuing the treatment; and/or c) adjusting dosage of the sodium pump inhibitor. For example, a decrease of sodium level close to or below the symptom-free sodium level would be a basis for discontinuing the treatment.

In some embodiments, the migraine rescue drug (such as sodium pump inhibitor) is administered in combination with other anti-migraine agents, such as other migraine rescue drugs described herein. As used herein, the term "anti-migraine agent" includes any pharmacological agent which may be used to treat or prevent migraine attacks (i.e., any pharmacological agent which may be used for the treatment or prophylaxis of migraine). For example, a sodium pump inhibitor can be co-administered with any of the following: anticonvulsants, antidepressants (such as amitriptyline, nortriptyline, and desipramine), beta-blockers, calcium channel blockers, nonsteroidal anti-inflammatory agents, serotonin receptor antagonists, serotonin reuptake inhibitors, serotonin noradrenaline reuptake inhibitors, analgesics, antiemetics, ergot derivatives, triptans, neuropeptide antagonists, and riboflavin (vitamin B2). The sodium pump inhibitor and the other anti-migraine agent can be administered simultaneously (either in the same composition or in separate compositions) or sequentially, i.e., the sodium pump inhibitor may be administered prior to or after the administration of the other anti-migraine agent.

Also provided herein are methods of screening individuals who may be suitable for receiving treatment with a migraine rescue drug (such as a sodium pump inhibitor) based on assessment of CSF sodium level or brain extracellular fluid level, methods of monitoring the treatment with migraine rescue drug (such as a sodium pump inhibitor) based on assessment of CSF sodium level or brain extracellular fluid sodium level, methods of determining responsiveness of individual for treatment with migraine rescue drug (such as sodium pump inhibitor) based on assessment of CSF sodium level or brain extracellular fluid level, and methods of determining length (i.e., defining therapeutic window) of the treatment based on assessment of CSF sodium level or brain extracellular fluid level.

Methods of Determining Predisposition to the Development of Migraine

Methods of determining predisposition of an individual to the development of migraine are also provided. By "predisposition" is meant an enhanced likelihood or greater probability of manifesting a particular pathology. "Development of migraine" refers to exhibition of one or more symptoms of a migraine attack, and/or other migraine-associated symptoms including, but not limited to, depression, mental confusion, personality change, mood change, fluid retention, and yawning.

Brain Tolerance Test

In one aspect, the invention provides a "brain tolerance test" for determining the predisposition of an individual to the development of migraine. Typically, the individual for the brain tolerance test does not exhibit any symptom of migraine at the time of the testing. The individual is then subject to a challenging condition that is sufficient to trigger migraine (such as administration of a sufficient amount of a challenging agent). The CSF or brain extracellular fluid sodium level in the individual is then monitored.

Accordingly, in some embodiments, there is provided a method of determining predisposition of an individual to the development of migraine, comprising: a) subjecting the individual to a challenging condition sufficient to trigger migraine at a symptom free stage; b) monitoring the CSF sodium level (or brain extracellular fluid sodium level) in said individual for a certain period of time, wherein a characteristic change in the CSF sodium level (or brain extracellular fluid sodium level) in the individual is indicative that the individual is predisposed to the development of migraine. In some embodiments, the method comprises: a) administering a sufficient amount of a challenging agent to the individual at a symptom free stage; b) monitoring the CSF sodium level (or brain extracellular fluid sodium level) in said individual for a certain period of time, wherein a characteristic change in the CSF sodium level (or brain extracellular fluid sodium level) in the individual is indicative that the individual is predisposed to the development of migraine.

In some embodiments, there is provided a method of determining predisposition of an individual to the development of migraine, comprising monitoring the CSF sodium level (or brain extracellular fluid sodium level) in said individual for a certain period of time, wherein said individual has been subject to a challenging condition sufficient to trigger migraine at a symptom free stage, and wherein a characteristic change in the CSF sodium level (or brain extracellular fluid sodium level) in the individual is indicative that the individual is predisposed to the development of migraine. In some embodiments, there is provided a method of determining predisposition of an individual to the development of migraine, comprising monitoring the CSF sodium level (or brain extracellular fluid sodium level) in said individual for a certain period of time, wherein the individual has been administered with a sufficient amount of a challenging agent at a symptom free stage, and wherein a characteristic change in the CSF sodium level (or brain extracellular fluid sodium level) in the individual is indicative that the individual is predisposed to the development of migraine.

The method may further include the step of measuring a baseline sodium level prior to, during, or immediately after (for example, within any of 1, 2, 3, 4, 5, 6, 7, 8, 9, or 10 minutes) subjecting the individual to the challenging condition or administering the challenging agent to the individual.

In some embodiments, the test is repeated by subjecting the individual to a variety of (such as two, three, four, five, six, or more) different conditions before a conclusion on the individual's predisposition to migraine is drawn. In some embodiments, the individual is tested against a panel of (such as two, three, four, five, six, or more) different challenging agents. For example, the brain tolerance test may be repeated using different challenging agents before a conclusion on the individual's predisposition to migraine is drawn. In some embodiments, a combination of different challenging agents is administered to the individual in a single brain tolerance test. In some embodiments, administration of a challenging agent is combined with a different challenging condition described herein in a brain tolerance test.

As described above, the CSF sodium level can be based on sodium concentration in the CSF or a body fluid whose sodium level correlates with that of the CSF (such as saliva, tear, sweat, and nasal discharge). In some embodiments, the CSF sodium level is based on sodium concentration in the saliva. In some embodiments, the CSF sodium level is based on the intracranial CSF sodium concentration (for example the intracranial CSF sodium concentration as determined by brain magnetic resonance spectrometry). Changes in CSF sodium level can be based on changes in the molar ratio of sodium and another analyte in the CSF, saliva, or other body fluids described herein. In some embodiments, the brain extracellular fluid sodium level is based on regional brain tissue sodium level, for example as determined by brain magnetic resonance spectrometry.

"A challenging condition sufficient to trigger migraine" refers to a condition that is known to trigger migraine in a group (such as two or more) of individuals under similar conditions. In some embodiments, the challenging condition is known or suspected to cause one or more symptoms of migraine (such as headache) in the individual being tested. Conditions that are known to trigger migraine are known in the art. For example, suitable challenging conditions include, but are not limited to, fasting, sleep deprivation, visual stimulation such as flickering light and fluorescent light, auditory challenge such as loud noises, olfactory challenges such as incense, tobacco smoke, and perfume, challenging agents as further described below, and various combinations thereof.

A challenging agent is administered "in a sufficient amount" if it is administered at a concentration that is known to trigger migraine in a group (such as two or more) of individuals under similar conditions. In some embodiments, the challenging agent is administered orally. In some embodiments, the challenging agent is administered intravenously. In some embodiments, the challenging agent is administered nasally.

Any agent that triggers migraine can be used as a challenging agent in the methods of the present invention. The challenging agent can be in any forms, including for example gas, solid, or liquid. In some embodiments, the challenging agent is known or suspected to cause one or more symptoms of migraine (such as headache) in the individual to be tested. Suitable challenging agents for methods of the present invention include, but are not limited to, estrogen and nitroglycerin. For example, in some embodiments, a sufficient amount of estrogen (for example in an amount about any of 0.2, 0.4, 0.45, 0.5, 0.6, 0.625, or 0.7 mg) can be administered. In some embodiments, a sufficient amount of nitroglycerin (for example in lingual spray of about any amount of 200, 300, 400, 500, 600, 700, 800, 900, or 1000 μg) can be administered.

In some embodiments, monitoring of CSF or brain extracellular fluid sodium level starts immediately after subjecting the individual to a challenging condition (such as administration of the challenging agent). In some embodiments, monitoring of sodium level starts within about any of 5, 10, 15, 20, 30, 40, 50, 60 minutes after the subjecting the individual to a challenging condition (such as administration of the challenging agent). In some embodiments, the monitoring is continuous, i.e., the measurement of the sodium level is carried out continuously (for example, in the case of brain magnetic resonance spectrometry). In some embodiments, sodium levels are measured less frequently, for example, in time intervals of at least about any of 5, 10, 15, 20, 25, 30, 40, 50, 60, or more minutes.

The total time period for determining the sodium level can vary, but is typically less than about 8 hours, such as less than about any of 7, 6, 5, 4, 3, 2 and 1 hour(s). In some embodiments, less time is required before a characteristic change in sodium level is observed. For example, sodium level can be monitored for less than about any of 0.1, 0.2, 0.3, 0.4, 0.5, 0.6, 0.7, 0.8, or 0.9 hours. In some embodiments, sodium level is determined at one single predetermined time point, such as at the end of any of 1, 2, 3, 4, 5, 6, 7, 8, or more hours.

In some embodiments, an increase in sodium level within a certain time period (for example, within any of 0.1, 0.2, 0.3, 0.4, 0.5, 0.6, 0.7, 0.8, 0.9, 1, 2, 3, 4, or 5 hours) is indicative that the individual is predisposed to the development of migraine. In some embodiments, an initial drop in sodium level followed by an increase in sodium level is indicative that the individual is predisposed to the development of migraine. For example, in some embodiments, the sodium level is dropped in the first 0.5 to 1 hour, followed by a rise in sodium level in the next 2, 3, 4, 5, 6, 7, or 8 hours.

In some embodiments, a characteristic change in sodium level is determined by comparing the sodium levels with a standard profile established based on the sodium levels of an challenged individual who is known not to be predisposed to the development of a migraine attack (as determined by traditional diagnostic methods or methods described herein). In some embodiments, the standard profile is established based on the sodium levels of two or more challenged individuals who are known not to be predisposed to the development of a migraine attack.

The brain tolerance test is generally (but not necessarily) tested during a time period of a day when the sodium level is stable in a normal individual not exhibiting a symptom of migraine. For example, in some embodiments, the brain tolerance test is carried out during the time period of from about 6 AM to about 6 PM. In some embodiments, the brain tolerance test is carried out during the time period of from about 1 PM to about 6 PM.

Determination Based on Comparison with a Threshold Level

In another aspect, there is provided a method of determining whether an individual is predisposed to the development of migraine based on comparison of the CSF sodium level (or brain extracellular fluid sodium level) in the individual with a threshold level. We have observed that the CSF sodium levels of migraineurs are statistically higher than those of nonmigraineurs. Thus, an increased CSF sodium level (or brain extracellular fluid sodium level) in an individual as compared to that of nonmigraineurs, which represents the threshold level, is indicative that the individual is predisposed to the development of migraine.

Accordingly, in some embodiments, there is provided a method of determining whether an individual is predisposed to the development of migraine, comprising determining CSF sodium level (or brain extracellular fluid sodium level) in said individual (referred herein as "test sodium level"), wherein a CSF sodium level (or brain extracellular fluid sodium level) above a threshold level is indicative that the individual is susceptible to the development of migraine.

In some embodiments, there is provided a method of determining predisposition of an individual to the development of migraine, comprising: a) determining the CSF sodium level (or brain extracellular fluid sodium level) in said individual, and b) comparing the CSF sodium level (or brain extracellular fluid sodium level) of the individual with a threshold level, wherein an increase in the CSF sodium level (or brain extracellular fluid sodium level) above a threshold level is indicative that the individual is predisposed to the development of migraine. In some embodiments, there is provided a method of determining predisposition of an individual to the development of migraine, comprising: a) comparing the CSF sodium level (or brain extracellular fluid sodium level) of the individual with a threshold level, and b) determining whether the individual is predisposed to the development of migraine based on an increase in the CSF sodium level (or brain extracellular fluid sodium level) above the threshold level. In some embodiments, there is provided a method of providing information for determining predisposition of an individual to the development of migraine, comprising: a) determining the CSF sodium level (or brain extracellular fluid sodium level) in said individual, and b) providing information about the CSF sodium level (or brain extracellular fluid sodium level) of the individual, wherein an increase in the CSF sodium level (or brain extracellular fluid sodium level) above a threshold level is indicative that the individual is predisposed to the development of migraine.

As used herein, a "threshold level" refers to the CSF sodium level (or brain extracellular fluid sodium level) in an individual who is known not to be predisposed to the development of a migraine (as determined by traditional diagnostic methods or methods described herein). In some embodiments, the threshold sodium level is based on the sodium levels of two or more individuals who are known not to be predisposed to the development of a migraine attack.

The test and threshold sodium levels may be made at the same time of a day, or during the same time period of a day when the sodium level is stable in a normal individual not exhibiting a symptom of migraine. For example, in some embodiments, both the test and the threshold sodium levels are determined during the time period of about 6 AM to about 6 PM. In some embodiments, both the test and the threshold sodium levels are determined during the time period of any of about 1 PM to about 6 PM, about 1 PM to about 5 PM, or about 2 PM to about 4 PM. In some embodiments, a threshold level is established several days, several weeks, several months, or even several years before determination of the test sodium level. In some embodiments, a series of threshold levels are established by measuring sodium levels at different time points of a day and, depending on the timing of the measurement of the test sodium level, a corresponding threshold level can be chosen for the comparison.

In some embodiments, the CSF sodium level is based on the sodium concentration in the CSF. For example, in some embodiments, an increase in CSF sodium concentration by at least about 0.5 mmol/L, such as at least about any of 0.5 mmol/L, 0.6 mmol/L, 0.7 mmol/L, 0.8 mmol/L, 0.9 mmol/L, 1.0 mmol/L, 2.0 mmol/L, 3.0 mmol/L, 4.0 mmol/L, or more is indicative of a predisposition to the development of migraine. In some embodiment, an increase in CSF sodium concentration by at least about 1 mmol/L is indicative of predisposition to the development of migraine. In some embodiments, the increase in sodium level is based on the increase in ratio of the CSF sodium concentration to concentration of another analyte in the CSF. In some embodiments, the increase in CSF sodium level is based on the increase in molar ratio of sodium to potassium ions in the CSF. In some embodiments, the increase in CSF sodium level is based on the increase in molar ratio of sodium to calcium ions in the CSF. In some embodiments, the increase in CSF sodium level is based on the increase in molar ratio of sodium to magnesium ions in the CSF. In some embodiments, the increase in CSF sodium level is based on the increase in ratio of the sodium concentration and the total protein concentration in the CSF. In some embodiments, the increase in CSF sodium level is based on the increase in ratio of the sodium concentration and the concentration of a particular protein in the CSF, such as albumin, immunoglobulin, transferrin, α-1-antitrypsin, and transthryretin. Other analytes in the CSF are also contemplated.

In some embodiments, the CSF is taken from the lumbar site. In some embodiments, the CSF is taken from the cervical site. In some embodiments, the CSF is taken from the ventricular site. In some embodiments, the intracranial cerebrospinal sodium level is determined, for example, by brain magnetic resonance spectrometry.

The CSF sodium level can also be determined based on the sodium level in a body fluid which correlates with the CSF sodium level. For example, in some embodiments, the CSF sodium level is determined based on saliva sodium concentration. In some embodiments, an increase in saliva sodium concentration by at least about 0.5 mmol/L, such as at least about any of 0.5 mmol/L, 0.6 mmol/L, 0.7 mmol/L, 0.8 mmol/L, 0.9 mmol/L, 1.0 mmol/L, 2.0 mmol/L, 3.0 mmol/L, 4.0 mmol/L, 5.0 mmol/L, 6.0 mmol/L, 7.0 mmol/L, 8.0 mmol/L, 9.0 mmol/L, 10.0 mmol/L, or more is indicative of a predisposition to the development of migraine. In some embodiment, an increase in saliva sodium concentration by at least about 1 mmol/L is indicative of a predisposition to the development of migraine. In some embodiments, the increase in CSF sodium level is based on the increase in ratio of the sodium concentration to concentration of another analyte in the saliva. In some embodiments, the increase in CSF sodium level is based on the increase in molar ratio of sodium to potassium ions in the saliva. In some embodiments, the increase in CSF sodium level is based on the increase in molar ratio of sodium to calcium ions in the saliva. In some embodiments, the increase in CSF sodium level is based on the increase in molar ratio of sodium to magnesium ions in the saliva. In some embodiments, the increase in CSF sodium level is based on the increase in ratio of the sodium concentration and the total protein concentration in the saliva. In some embodiments, the increase in CSF sodium level is based on the increase in ratio of the sodium concentration and the concentration of a particular protein in the saliva, such as salivary amylase and lactoferrin. Other analytes in the saliva are also contemplated.

In some embodiments, the CSF sodium level is based on sodium concentration in a body fluid that is innervated by neuronal terminals originating from trigeminovascular system. In some embodiments, the increase in CSF sodium level is based on the increase of molar ratio of sodium to another analyte in a body fluid that is innervated by neuronal terminals originating from trigeminovascular system. For example, the sodium level can be based on sodium concentration in tear, saliva, sweat, nasal discharge, etc. In some embodiments, sodium level is based on sodium concentration in a body fluid that is produced by a gland of the neuroectoderm origin.

In some embodiments, the sodium level in the brain extracellular fluid is determined. Brain extracellular fluid sodium level can be determined, for example, based on regional brain tissue concentration, such as regional brain tissue concentration as determined by brain magnetic resonance spectrometry.

A similar kind of comparison as described above can be used for the diagnosis of chronic daily headache. "Chronic daily headache" refers to frequent headache in an individual with a frequency of about fifteen times per month or more. It is believed that individuals with chronic daily headache have an increased CSF sodium level and/or brain extracellular fluid sodium level as compared to a threshold level. Accordingly, in some embodiments, there is provided a method of diagnosing chronic daily headache in an individual having headache, comprising determining CSF sodium level (or brain extracellular fluid sodium level) in said individual, wherein an increase of CSF sodium level (or brain extracellular fluid sodium level) above a threshold level is indicative that the individual is having a chronic daily headache. For example, an increase of CSF sodium level by at least about any of 0.5%, 1%, 2%, 3%, 4%, 5%, 6%, 7%, 7.5%, or more is indicative of a chronic daily headache. In some embodiments, an elevated CSF sodium level for at least about any of 3, 6, 9, 12, 15, or more days is indicative of a chronic daily headache. In some embodiments, an elevated sodium level for at least about any of 5, 10, 15 or more days in a 30 day period (either continuously or non-continuously) is indicative of a chronic daily headache.

Also provided are methods of treating an individual diagnosed with chronic daily headache by method described above by administering an effective amount of drugs for treatment of chronic daily headache, such as migraine rescue drugs described herein.

Determination of Sodium Levels

Methods described above generally require measurement of sodium levels. In vitro and in vivo methods of determining sodium levels are known in the art. For example, sodium level in a body fluid (such as CSF and saliva) can be determined by any one or more of the following: mass spectrometry, flame photometry, atomic absorption spectrometry, single quantum sodium nuclear magnetic resonance (Na NMR), multiple quantum filtered Na NMR, sodium magnetic resonance spectrometry, sodium magnetic resonance imaging, electron probe microanalysis, ion-selective electrode, ion chromatography, inductively coupled plasma emission mass spectrometry (ICP/MS), and ion probes (such as ion sensitive chelating agents and ion sensitive dyes). Determination of sodium level can be repeated one or more times (for example by the same or different methods) to ensure accuracy of the measurements.

In some embodiments, sodium level is determined by using a fluorescent or color ion probe which fluoresces or changes color under light or a particular wavelength. For example, suitable sodium ion probes include SBFI (sodium-binding benzofuran isophthalate), SBFO, and sodium green. The sensitivity of the sodium ion probes may be adjusted, for example, by varying the concentration of the ion probe.

In some embodiments, sodium level is determined by using a lifetime-based sensing method described in U.S. Pat. No. 6,742,221. Briefly, the method uses a photoluminescent ligand probe having intrinsic sodium-induced lifetime changes. The probe is non-covalently bound to the ionic solute to form a sodium-bound and unbound species wherein the bound and unbound species of the probe exist in the sample. The sample is excited with radiation and the resulting emission beams from the bound and unbound species are detected. The apparent luminescence lifetime of the emission is calculated to determine concentrations of sodium in the sample.

In some embodiments, sodium level is determined in vivo by methods such as NMR and brain magnetic resonance spectrometry.

Kits and Devices

Also provided herein are kits and devices that are useful for methods of the present invention.

In some embodiments, there is provided a device for measuring sodium level in a body fluid (such as CSF and/or saliva sodium concentration) comprising a sodium detector for measuring and/or indicating sodium level in a body fluid (such as CSF and/or saliva). In some embodiments, the device further comprises a body fluid collector. In some embodiments, the device is useful for the diagnosis of migraine attack. In some embodiments, the device further comprises an indicator that indicates the presence or absence of a migraine attack. In some embodiments, the device is useful for determining predisposition of an individual to the development of migraine. In some embodiments, the device further comprises an indicator that indicates the presence or absence of a predisposition to the development of migraine.

In some embodiments, the sodium detector comprises an ion-selective electrode. In some embodiments, the sodium detector comprises an ion probe (such as ion sensitive chelating agents or ion sensitive dyes). In some embodiments, the sodium detector comprises a fluorescent or color ion probe such as SBFI, SBFO, and sodium green.

Also provided are kits for methods described herein. In some embodiments, the kit comprises a device for determining sodium level in a body fluid (such as CSF and/or saliva sodium concentration) and instruction for using the device to carry out methods of the present invention.

In some embodiments, there is provided a kit for treating migraine attack comprising a device for diagnosing migraine attack and a composition comprising a migraine rescue drug (such as sodium pump inhibitor). In some embodiments, the kit further comprises an instruction for carrying out a method of treatment described herein.

In some embodiments, there is provided a kit for determining predisposition of an individual to the development of migraine, comprising a) a sufficient amount of a challenging agent; and b) a device that determines sodium concentration in a body fluid (such as CSF and/or saliva) of the individual. In some embodiments, the kit further comprises an instruction for using of the challenging agent and the device in conjunction methods of the present invention.

In some embodiments, there is provided a kit for determining predisposition of an individual to the development of migraine, comprising a device that determines sodium concentration in body fluid (such as CSF and/or saliva) and a standard sample that provides a threshold sodium level. In some embodiments, the kit further comprises an instruction for using the device and the standard sample for method of the present invention.

The following Examples are provided to illustrate, but not limit, the invention.

EXAMPLE 1

This example shows correlation between increased sodium concentration in CSF and migraine attack or predisposition to develop migraine.

Selection of Patients for the Study

We recruited twenty migraineurs for this study. We recorded lifetime histories of all participants' troublesome headaches, and diagnosed each headache type using the International expertise (RPC & MGH), and reached consensus with a validated, structured interview and computerized classification. To reduce clinical heterogeneity, we selected only those classified with "migraine without aura" as a primary headache problem. Those with additional primary headache disorders of migraine or tension-type that were less frequent were not excluded. Migraineurs self-reported their headache frequency, severity, and duration by structured interview and, to further restrict clinical heterogeneity, we included only those with a minimum of 1 attack/year and a maximum frequency of 10 days/months.

We recruited volunteer controls who stated that they did not suffer from troublesome headaches and then administered a different structured interview to rate and record their headache histories. Controls were accepted for the study only if their answers to the headache interview did not meet IHS criteria for headache of any type, they revealed no headache propensity, and they had no family history of migraine. After this assessment, four of the initial applicants were excluded due to previously undiagnosed migraine (n=3) or sinus headache (n=1).

For both migraineurs and controls, all maintenance therapy was unchanged for more than 30 days prior to sampling; sleep, diet (including alcohol/caffeine), and stress levels were unchanged and catastrophic events had not been experienced within the 24 hours prior to lumbar puncture. Subjects were excluded if rescue medications for headache were taken within 24 hours prior to sampling or if lumbar puncture could not be performed due to fever, bleeding disorder, coumadin treatment, pregnancy, or other acute medical conditions.

Migraineurs sampled in MH− were defined as having no headache (0 of 10) for more than 24 hours at lumbar puncture (LP). Migraineurs in MH+ were defined according to the following criteria: severity at time of LP of >5 on a scale of 0 to 10 (headache duration was noted); IHS diagnostic classification of 1.1.1 of the headache state(s) at the time of the study; clinician differentiated between a 1.1.1 attack and other types, when relevant, and the headache was spontaneous and typical for each person; all prescription and over-the-counter medications as well as supplements recorded for 30 days before sampling; and all maintenance and rescue therapy unchanged for more than 30 days prior to LP.

Sample Collection and Assays

To minimize diurnal fluctuations, we collected CSF between 1 pm and 6 pm in the lateral or sitting position using a 20/22 gauge Quincke type needle between the L3/4 or L2/3 positions. We drip collected the CSF in three consecutive 6-7 mL fractions, centrifuged each at 3000×g to pellet cells, and stored 1 mL aliquots of the CSF supernatant at −80° C. until thawed for assay, after taking an aliquot of 10 μL for total protein assay.

Blood was collected at the time of LP in potassium EDTA tubes by venipuncture from the anticubital fossa, and plasma was separated by centrifugation (5,000 g for 3 min), aliquoted and stored at −80° C. until thawed for assay. An aliquot of 10 μL was taken for total protein assay (see below) and urea and creatinine were measured using a chemical autoanalyzer.

Concentrations of protein in CSF were determined using a micro titer plate-based Coomassie protein assay using human serum albumin (Sigma), 0-100 μg/mL, as a standard. Briefly, 5 μL of diluted CSF (10× and 100×) was added to a 96 well microtiter plate in triplicate. Coomassie dye (BioRad, Hercules, Calif.) was diluted (5×) and 200 μL was added to each well. After 5 min, the OD at 595 nm was obtained using a microplate reader (Molecular Devices, Sunnyvale, Calif.) and protein concentrations in each sample were computed using Softmax software from Molecular Devices.

Ions were all measured, without knowledge of the diagnosis, from 300 μL of fluid that came from the first CSF fraction and from 300 μL of blood plasma. $Na^+$ and $K^+$ levels were determined using a Roche/Hitachi Modular analyzer. The ion-selective electrode module employed electrodes of the liquid/liquid junction type that are based on neutral carriers. Imprecision studies conducted according to NCCLS guidelines yielded a within-run CV of 0.2% for both $Na^+$ and $K^+$. Ionized calcium was measured on a Bayer/Chiron 634 analyzer using an electrode based on an ion exchanger, with a typical within-run precision CV of 1%. Total Ca and Mg levels were determined on the Roche/Hitachi Modular analyzer by colorimetric endpoint methods: o-cresolphthalein binds with total Ca with a within-run precision CV of 0.9%; xylidyl blue binds with total Mg with a within-run precision CV of 1.2%. Normal values for CSF $Na^+$ for this laboratory are 135-145 mmol/L. Osmolality was determined by depression of freezing point (Advanced Instruments, Inc.).

Prescription drug usage between migraineurs and controls was compared using the Mann Whitney test. We compared $Na^+$, $K^+$, $Ca^{2+}$, and total Ca and Mg concentrations among all three clinical groups (MH+, MH−, and C) using analysis of variance. We used repeated measures methods for comparisons within subjects of MH+ and MH−, and Dunn's Method for pairwise comparisons. All tests were two-sided and used a 0.05 significance level.

Results

We assessed 20 migraineurs with the IHS diagnosis of 1.1.1 (migraine without aura) and 11 non-headache suffering controls. Of the 20 migraineurs, 10 were sampled in MH−, 6 were sampled in MH+, and 4 were sampled in both MH+ and MH−. While some of the migraineurs had additional primary headache conditions in their lifetime histories, migraine without aura (1.1.1) was the dominant headache for all included in the study.

Increased prescription drug usage was reported by migraineurs, mainly for anti-migraine treatments, and these included drugs known to act on ion channels (topiramate, gabapentin, valproate, verapamil). Average per person usage of all prescription drugs and identification of those known to have effects on cations are itemized in Table 1.

TABLE 1

Cation-impacting prescription medication usage in migraineurs and controls

| Drug | # Migraineurs n = 20 | # Controls n = 11 |
|---|---|---|
| Hydrochlorothiazide | 1 | 1 |
| Gabapentin | 1 | 1 |
| Verapamil | 1 | 0 |
| Topiramate | 5 | 0 |
| Valproate | 1 | 0 |
| No medication | 3 | 5 |
| Mean (SD) # of drugs taken per subject * | 4.8 (4.4) | 1.5 (1.7) |

(* $p < 0.05$ by Mann Whitney)

Migraineurs made no change in their prescription drug usage between their MH+ and MH− samplings. The four migraineurs sampled in both MH+ and MH− had no change in medication throughout the study: two were not taking any medication, a third was taking topiramate, and the fourth was taking valproate, but neither of the latter two made any change in therapy for three months prior to or during the study.

Our initial studies examined protein concentrations in CSF to determine whether any changes could be due to blood/brain compartment disruption. Protein concentrations in C (26.8±13.5 mg/dL, n=11) did not differ significantly from concentrations in MH+ (28.7±6.7 mg/dL, n=6) or MH− (29.5±9.7 mg/dL, n=10). Thus, there is no evidence of plasma leakage or contamination of the CSF in these sample groups. CSF osmolality did not differ among C, MH+, and MH−, consistent with no fluid shift between the CSF, blood, and brain tissue compartments. There were no differences in blood plasma urea or creatinine concentrations among the C, MH+, and MH− (data not shown), consistent with no change in renal function, nutritional status, or hydration.

The most general and direct determinants of ion channel and pump activities are the concentrations of their substrates, the ions themselves. CSF $Na^+$ levels differed significantly by clinical group (Table 2). Pairwise comparison revealed that the differences are between the MH+ and both the MH− and C groups. CSF $Na^+$ in MH− was 1 mmol/L higher than that in C.

TABLE 2

Mean (±SD) of CSF and plasma $Na^+$ levels in migraine states (MH+ and MH−) and controls (C)

| Clinical state | CSF $Na^+$ (mmol/L) | Plasma $Na^+$ (mmol/L) |
|---|---|---|
| MH+ (n = 6) | 149 ± 2 ** | 136 ± 5 |
| MH− (n = 10) | 146 ± 2 | 135 ± 2 |
| C (n = 11) | 145 ± 4 | 135 ± 2 |

(** $p < 0.005$ by ANOVA)

We then analyzed a subgroup of four migraineurs in both MH+ and MH−. Two were on no therapy, and two were taking a stable maintenance dose of drugs that influence sodium (topiramate or valproate). Repeated measures comparison of their MH+ and MH− CSF $Na^+$ levels revealed they had higher $Na^+$ in MH+ than in MH− (Table 3), supporting the result from the total study population.

TABLE 3

Mean (±SD) CSF $Na^+$ levels in paired samples of migraineurs in MH+ and MH− states (n = 4)

| Clinical state | CSF $Na^+$ (mmol/L) |
|---|---|
| MH+ | 148 ± 2 * |
| MH− | 146 ± 1 |

(* $p < 0.05$ by repeated measures)

To determine if the CSF changes were a reflection of systemic levels, we measured blood plasma concentrations. There were no differences in the $Na^+$ from blood plasma (obtained at the same time that the CSF was collected) between the MH+, MH− and the C groups (Table 2).

To determine whether changes were specific for sodium, we measured the monovalent ion, $K^+$ in CSF. $K^+$ was similar in the MH+, MH− and C groups, (Table 4). To further define the specificity of the changes, we determined the concentrations of the two divalent cations, $Mg^{2+}$ and $Ca^{2+}$. There were no differences in total calcium, ionized calcium; or total magnesium between the MH+, MH− and C groups, as shown in Table 4.

TABLE 4

Means (±SD) of other CSF cation concentrations in migraine states (MH+ and MH−) and controls (C)

| Clinical state | CSF $K^+$ (mmol/L) | Total CSF Ca (mg/dL) | Ionized CSF $Ca^{2+}$ (mmol/L) | Total CSF Mg (mg/dL) |
|---|---|---|---|---|
| MH+ (n = 6) | 2.8 ± 0.1 | 4.45 ± 0.34 | 0.58 ± 0.08 | 2.64 ± 0.18 |
| MH− (n = 10) | 2.8 ± 0.1 | 4.54 ± 0.44 | 0.62 ± 0.12 | 2.58 ± 0.04 |
| C (n = 11) | 2.7 ± 0.2 | 4.36 ± 0.28 | 0.60 ± 0.08 | 2.59 ± 0.06 |

Together, these data suggest that the Na+ changes are specific and not associated with changes in these other common mono- or divalent ions.

CONCLUSIONS

Our data suggest that changes in CSF sodium concentration are specific and selective for migraineurs without aura. The absence of significant CSF changes of total Ca and Mg, ionized Ca2+, and K+ highlights the singular finding of this observed Na+increase in CSF. The lack of change in osmolality suggests there is no fluid shift.

The difference in CSF Na+ between MH+ and MH− suggests that this is an ictus-specific change of migraine. That these findings appear to persist in the four migraine participants who were analyzed in both states restricts the interpretation more emphatically to their ictal event and removes the possibility that their drug treatment was responsible since these subjects acted as their own controls and had no change in medication or other clinical state between sampling.

The lack of Na+change in the blood plasma of all clinical groups strongly suggests that this CSF increase is not due to peripheral/dietary origin but is generated from the brain. Furthermore, there was no evidence that our participants had peripheral dehydration (based on blood urea and creatinine) that could increase CSF Na+. CSF Na+ equilibrates in less than two hours between blood and CSF, and the brain/extracellular fluid/CSF equilibrates much more rapidly, especially in mobile subjects. Thus we can confidently assume that the observed change in CSF reflects a similar level in brain extracellular fluid.

CSF sodium levels are known to be carefully regulated, and the 3 mmol/L Na+ increase that we observed in MH+ reflects a migraine process that is still tightly regulated, as distinct from a systemic hypernatremic crisis. Increased extracellular Na+ has been shown to affect the inactivating peptide on voltage-gated sodium channels, directly replacing it from the extracellular orifice of the channel. While the resting membrane potential is mainly derived from the K+ gradient across the membrane (unchanged in the CSF in our study), an increased extracellular sodium in MH+ will slightly reduce the threshold for repetitive neuronal firing by increasing sodium conductance, increase pH-induced nociceptor discharge, and alter coincidence detection in medial superior olivary neurons. These effects in humans would contribute to a substantial neural disturbance.

Such neural disturbance from increased extracellular Na+ are directly consistent with the main clinical features of migraine: pain, photophobia, phonophobia, osmophobia, nausea, vomiting, and confusion.

The mean Na+ level in MH− is just 1 mmol/L above the level of the control group. This may represent a predisposition for the migraineur such that additional provocation transition them more easily to MH+.

EXAMPLE 2

This example shows correlation between an increased sodium concentration in saliva with migraine attack.

Unstimulated saliva was obtained by spitting method during 1 PM to 5 PM from a single study participant. The participant was first asked to expectorate his mouth of saliva and rinse the mouth with deionized water. He was then asked to dribble saliva from the front of the mouth into a plastic tube for five to ten minutes, avoiding mucus from the back of the mouth. Duration of time is noted for calculation of flow rate. Sodium concentration was determined using ion selective electrode.

For the individual tested, the sodium concentration at the headache free stage is 5 mmol/L and at severe headache stage at same time of day is 9 mmol/day. This high sodium during headache mirrors that of the high CSF sodium during headache.

EXAMPLE 3

This example shows correlation between an increased sodium concentration in CSF and saliva with migraine attack in an individual.

CSF and saliva samples were taken from the individual at MH+ state and MH− state as described above. The saliva sample was further processed by using 5 µL of glacial acetic acid per 500 µL of saliva to precipitate mucin and protein. A white, stringy precipitate usually formed, and was pelleted at 5,000 rpm for 10 mins. The supernatant was carefully removed, aliquoted and frozen for later analysis. This method did not alter the sodium level and allowed pipetting of saliva without stringy mucin.

Sodium concentrations in both the CSF and the processed saliva samples were determined using ion chromatography method. See e.g., Qiu et al., 2005, *J. Chromatogr. A.* 1073(1-2):263-7. Briefly, a Dionex HPLC device was used for the assay. The device included a DX500 system with an IP25 isocratic pump, an EG40 eluent generator with methyl sulfonic acid, an ULTRA cation self-regenerating suppressor, and a CD 20 conductivity meter. We ran a standard curve of sodium (NIST-certified) followed by unknown samples, with a new standard curve every 10-20 samples.

The CSF sodium concentration of the individual at MH+ state was 150.13 mmol/L. The CSF sodium concentration of the individual at MH− state was 146.95 mmol/L. The saliva sodium concentration of the individual at MH+ state was 8 mmol/L. The saliva sodium concentration of the individual at MH− state was 3 mmol/L.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of diagnosing migraine in an individual exhibiting one or more symptoms of a migraine attack, comprising:
   a) determining cerebrospinal fluid (CSF) or brain extracellular fluid sodium level of the individual; and
   b) comparing the CSF or brain extracellular fluid sodium level in the same individual at a symptom-free stage, wherein an increase in CSF or brain extracellular sodium level above the level at a symptom-free stage is indicative of a migraine attack.

2. The method of claim 1, wherein the diagnosis is based on the CSF sodium level.

3. The method of claim 2, wherein the CSF sodium level is based on the sodium concentration in the CSF of the individual.

4. The method of claim 3, wherein an increase in sodium concentration in the CSF by at least about 3 mmol/L is indicative of a migraine attack.

5. The method of claim 2, wherein the increase in CSF sodium level is based on the increase in sodium to potassium ion molar ratio in the CSF of the individual.

6. The method of claim 2, wherein the CSF sodium level is intracranial CSF sodium level.

7. The method of claim 6, wherein the intracranial CSF sodium level is based on sodium concentration determined by brain magnetic resonance imaging.

8. The method of claim 1, wherein the diagnosis is based on the brain extracellular fluid sodium level.

9. The method of claim 8, wherein the brain extracellular fluid sodium level is based on the regional brain tissue sodium concentration determined by brain magnetic resonance imaging.

10. A method of treating or continuing to treat migraine attack in an individual exhibiting one or more symptoms of migraine attack, wherein the individual is diagnosed as having migraine attack by the method of claim 1, comprising: administering to the individual an effective amount of a sodium pump inhibitor.

11. The method of claim 10, wherein the sodium pump inhibitor is steroid glycoside.

12. The method of claim 11, wherein the steroid glycoside is ouabain.

13. The method of claim 11, wherein the steroid glycoside is digoxin.

14. The method of claim 10, wherein a single dose of the sodium pump inhibitor is administered.

15. A method for determining predisposition of an individual to the development of migraine, comprising:
    a) administering a sufficient amount of a challenging agent to the individual at a symptom free stage; and
    b) monitoring cerebrospinal fluid (CSF) or brain extracellular fluid sodium level in said individual for a certain period of time,
    wherein a characteristic change in the CSF or brain extracellular fluid sodium level in the individual is indicative that the individual is predisposed to the development of migraine.

16. The method of claim 15, further comprising the step of determining a baseline CSF or brain extracellular fluid sodium level in the individual prior to, during, or immediately after administering the challenging agent.

17. The method of claim 15, wherein an increase in the CSF or brain extracellular fluid sodium level above a baseline level after a certain time period is indicative that the individual is predisposed to the development of migraine.

18. The method of claim 15, wherein an initial drop of the CSF or brain extracellular fluid sodium level below a baseline level followed by a subsequent increase in the CSF or brain extracellular fluid sodium level above the baseline level is indicative that the individual is predisposed to the development of migraine.

19. The method of claim 15, wherein the determination is based on CSF sodium level.

20. The method of claim 19, wherein the CSF sodium level is based on the sodium concentration in the CSF of the individual.

21. The method of claim 19, wherein the change in CSF sodium level is based on the change in sodium to potassium ion molar ratio in the CSF of the individual.

22. The method of claim 15, wherein the determination is based on brain extracellular fluid sodium level.

23. The method of claim 22, wherein the brain extracellular fluid sodium level is based on regional brain tissue sodium concentration determined by brain magnetic resonance imaging.

24. The method of claim 15, wherein the challenging agent is administered orally.

25. The method of claim 15, wherein the challenging agent is administered intravenously.

26. The method of claim 15, wherein the challenging agent is an agent that is known or suspected to induce headache in said individual.

27. A method for determining the predisposition of an individual to the development of migraine, comprising: determining cerebrospinal fluid (CSF) or brain extracellular fluid sodium level in said individual, wherein an increase of CSF or brain extracellular fluid sodium level above a threshold level is indicative that the individual is predisposed to the development of migraine.

28. The method of claim 27, wherein the determination is based on CSF sodium level.

29. The method of claim 28, wherein the CSF sodium level is based on the sodium concentration in the CSF of the individual.

30. The method of claim 28, wherein the increase in CSF sodium level is based on the increase in sodium to potassium ion molar ratio in the CSF of the individual.

31. The method of claim 27, wherein the determination is based on the brain extracellular fluid sodium level.

32. The method of claim 31, wherein the brain extracellular fluid sodium level is based on regional brain tissue sodium concentration determined by brain magnetic resonance imaging of the individual.

* * * * *